(12) United States Patent
Zehner et al.

(10) Patent No.: US 7,064,237 B2
(45) Date of Patent: Jun. 20, 2006

(54) METHOD FOR THE PRODUCTION OF AMINES

(75) Inventors: Peter Zehner, Ludwigshafen (DE); Joern Mueller, Bad Essen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 128 days.

(21) Appl. No.: 10/502,779

(22) PCT Filed: Feb. 4, 2003

(86) PCT No.: PCT/EP03/01063

§ 371 (c)(1),
(2), (4) Date: Jul. 28, 2004

(87) PCT Pub. No.: WO03/068724

PCT Pub. Date: Aug. 21, 2003

(65) Prior Publication Data

US 2005/0119505 A1    Jun. 2, 2005

(30) Foreign Application Priority Data

Feb. 15, 2002   (DE)   ................. 102 06 214

(51) Int. Cl.
*C07C 209/36*   (2006.01)

(52) U.S. Cl. ............... 564/417; 564/418; 564/421; 564/422; 564/423

(58) Field of Classification Search ................. None
See application file for complete search history.

(56) References Cited

FOREIGN PATENT DOCUMENTS

DE    198 44 901    11/1999
WO    00 35852    6/2000

*Primary Examiner*—Brian Davis
(74) *Attorney, Agent, or Firm*—Oblon, Spivak, McClelland, Maier & Neustadt, P.C.

(57) ABSTRACT

Amines are prepared by hydrogenation of the corresponding nitroaromatics in a vertical reactor whose length is greater than its diameter and which has in its upper region a downward-directed jet nozzle via which the reaction mixture and, if desired, part of the starting materials are introduced, has an outlet at any point on the reactor via which the reaction mixture is conveyed in an external circuit by means of a transport device back to the jet nozzle and has a flow reversal in its lower region, wherein at least part of the hydrogen and/or nitroaromatic starting materials used is fed into the liquid phase of the reactor in such a way that they travel upward in the liquid phase.

20 Claims, No Drawings

METHOD FOR THE PRODUCTION OF AMINES

The invention relates to a process for preparing amines by hydrogenation of the corresponding nitroaromatics.

The preparation of amines, in particular aromatic amines, by hydrogenation of the corresponding nitroaromatics has been known for a long time and is widely described in the literature.

In industry, the hydrogenation is usually carried out in the liquid phase using hydrogenation catalysts. Here, it is usual to mix the compound to be reduced in a solvent with the catalyst and to reduce it batchwise in an autoclave or continuously in a stirred tank, a loop reactor, a bubble column or a reactor cascade. The known processes of this type have a series of disadvantages, for example the necessity of discharging and in particular disposing of deactivated catalyst, which leads to catalyst losses. Furthermore, the secondary reactions which frequently occur and lead to the formation of troublesome substances, e.g. tar-like components, and thus to decreases in yield are a problem in many processes used hitherto.

WO 00/35852 describes a process for preparing amines by hydrogenation of the corresponding nitroaromatics, in which the reaction is carried out in a vertical reactor whose length is greater than its diameter and which has in its upper region a downward-directed jet nozzle via which the starting materials and the reaction mixture are introduced, has an outlet at any point on the reactor via which the reaction mixture is conveyed in an external circuit by means of a transport device back to the jet nozzle and has a flow reversal in its lower region. This reactor preferably has internal heat exchangers. The starting materials are preferably introduced via the jet nozzle to achieve very good mixing. The process described in WO 00/35852 enables the aromatic amines to be prepared in a high space-time yield and with substantial suppression of secondary reactions.

However, it has been found that increased contents of nitroaromatics sometimes occur in the reactor, particularly in the downward-directed flow below the flow reversal of the liquid phase, in particular in the vicinity of the outlet of the reactor, especially when using low catalyst contents.

DE-C-198 44 901 describes a process for preparing aromatic amines which is carried out in the upflow mode and in which the nitroaromatics are fed into the reactor via a perforated ring line. The ring line can also be cooled by means of an external heat exchanger in order to avoid the risk of overheating and thus thermal decomposition of the nitroaromatics. This process is said to achieve a particularly good distribution of the nitroaromatics in the reaction mixture. Reactors described as suitable are, for example, loop reactors, bubble columns and preferably stirred tanks. Reactors having an internal loop flow, as described in WO 00/35852, are not mentioned in this document. However, specifically in such reactors, the above-described enrichment of the liquid reaction mixture in nitroaromatics in the region below the flow reversal can occur. This can be because the residence time in the fast, downward-directed flow and in the region of the flow reversal at the impingement plate is too short for complete reaction of the nitroaromatics. Since the downward-directed flow is a fast-flowing mixture, the residence time in this part of the reactor is in any case very short. This effect occurs particularly when using low catalyst contents or catalysts having a low activity.

It is an object of the present invention to develop a process for preparing aromatic amines in a flow reactor, in which catalyst deactivation is avoided and by-product formation is reduced and no nitroaromatics are present at the outlet of the reactor and which can be operated using low catalyst concentrations.

We have found that this object is achieved by introducing at least part of the hydrogen and/or the nitroaromatics into the liquid phase of a reactor as described in WO 00/35852 in such a way that they flow upward in the liquid reaction mixture.

The present invention accordingly provides a process for preparing amines by hydrogenation of the corresponding nitroaromatics in a vertical reactor whose length is greater than its diameter and which has in its upper region a downward-directed jet nozzle via which the reaction mixture and, if desired, part of the starting materials are introduced, has an outlet at any point on the reactor via which the reaction mixture is conveyed in an external circuit by means of a transport device back to the jet nozzle and has a flow reversal in its lower region, wherein at least part of the hydrogen and/or nitroaromatic starting materials used is fed into the liquid phase of the reactor in such a way that they flow upward in the liquid reaction mixture.

The hydrogen can be introduced either into the upward-directed flow of the liquid phase in the reactor above the flow reversal or into the downward-directed flow of the liquid phase in the reactor below the flow reversal, since it flows upward in the liquid phase in any case because of its low density.

The nitroaromatics are introduced into the upward-directed flow within the liquid phase within the reactor, i.e. above the flow reversal.

In a preferred embodiment of the invention, the reactor has an impingement plate arranged perpendicular to the reactor wall in its lower part. In this embodiment, the nitroaromatics and, if desired, part or all of the hydrogen is/are introduced above the impingement plate into the upward-directed flow within the reactor. In a further preferred embodiment of the invention, the reactor is additionally provided with a concentric plug-in tube which is installed parallel to the reactor wall and through which the reaction mixture is guided from the jet nozzle to the flow reversal, in particular the impingement plate.

As indicated, the total amount of the hydrogen and of the nitroaromatics can be fed into the reactor as described.

It is likewise possible for either only the hydrogen or only the nitroaromatics to be fed into the reactor at the position provided for according to the invention and the other starting material to be introduced into the reactor exclusively at another point, preferably above the jet nozzle or by introduction into the external circuit. The hydrogen which is not fed into the reactor at the point provided for according to the invention can also be fed into the gas space of the reactor at any point. From there, it is pushed into the liquid phase of the reactor by the driving jet.

In a preferred embodiment of the process of the present invention, part of the hydrogen added is fed into the external circuit of the reactor. The hydrogen is preferably fed in on the suction side of the external circuit. The amount of hydrogen fed into the external circuit should be such that the reaction mixture in the external circuit has a gas content in the range from 3 to 15% by weight, preferably from 5 to 10% by weight. In this range, the reaction mixture can be supplied with sufficient hydrogen by optimum dispersion of the gas in the liquid reaction mixture. At higher gas contents in the ring line, problems with the circulation pump can occur, and lower gas contents in the ring line no longer have a positive effect on the reaction.

The introduction of the hydrogen at the point provided for according to the present invention can in the simplest case be carried out via one or more inlet tubes. Better distribution of the hydrogen can, for example, be achieved by use of a feed device having a plurality of openings. A distributor ring is preferably used on account of the construction of the reactor used for the process of the present invention. Other preferred devices for introducing the hydrogen are distributor stars or plates of sintered material.

The nitroaromatics can be introduced either at the point provided for according to the present invention or into the external circuit or preferably into the nozzle. Introduction into the external circuit is less preferred, since mixing is poorer there. Introduction into the nozzle can occur in the immediate vicinity of the outlet of the nozzle. Better mixing can be achieved if the nitroaromatics are introduced at the end of the nozzle adjoining the external pumped circulation line or into the external pumped circulation line directly at the nozzle.

The introduction of the nitroaromatics at the point provided for according to the present invention can likewise occur via inlet tubes, distributor stars, ring lines or other devices which allow good distribution of the nitroaromatics.

The device for introducing the nitroaromatics is, as indicated above, located in the lower part of the reactor above the flow reversal, and it has to be ensured that the nitroaromatics are fed into the upward-directed flow. The device for introducing the nitroaromatics is preferably installed between the impingement plate and the concentric plug-in tube.

The hydrogen is likewise fed into the lower part of the reactor so that it travels upward in the liquid reaction mixture. It is particularly preferably introduced between the bottom of the reactor and the plug-in tube.

When ring lines are used for the introduction of hydrogen and/or nitroaromatics at the point provided for according to the present invention, these have a number of holes which is sufficient for optimum distribution. This number is preferably in the range from 2 to 500, in particular from 2 to 200. When the starting materials flow through the holes, a pressure drop occurs. In the case of the nitroaromatics, this is preferably in the range from 0.1 to 10 bar, in particular from 0.3 to 3 bar, while in the case of hydrogen it is preferably in the range from 0.05 to 0.15 bar.

To avoid hazardous operating conditions in the case of nitroaromatics which can decompose thermally at the temperatures prevailing in the reactor, the mass flow into the introduction device should be monitored. When the mass flow decreases, the nitroaromatics have to be removed from the introduction device. This can be achieved, for example, by flushing with warm water. A further possible way of reducing the risk of thermal decomposition of the nitroaromatics is cooling the introduction device. This variant is not preferred for the process of the present invention, since the cooling jacket increases the cross section of the introduction device, which can have an adverse effect on the flow in the reactor.

Apart from the introduction of the starting materials, the reactor corresponds to the reactor described in WO 00/35852.

The jet nozzle of the reactor can be designed as a single-, two- or three-fluid nozzle. When all of the hydrogen and the total amount of nitroaromatics are fed in at the bottom, a single-fluid nozzle is preferred. In the case of the single-fluid nozzle, only the liquid reaction mixture is fed in through the nozzle and the hydrogen and the nitroaromatics are introduced into the reactor at the preferred points. An advantage of this embodiment is the simple construction of this nozzle, but it has the disadvantage of poorer dispersion of the hydrogen in the reaction mixture. In the case of two- or three-fluid nozzles, which have a more complicated construction, the hydrogen and also the nitroaromatics can be introduced through the middle of the nozzle or via the annular gap and be dispersed. In this embodiment of the process, dispersion of the hydrogen in the reaction mixture is significantly better.

Depending on the type of nitro compounds used, preference is given to maintaining a pressure of from 5 to 100 bar, more preferably from 10 to 50 bar, and an operating temperature of from 80 to 200° C., more preferably from 100 to 150° C., in the reactor. The power input at the nozzle is preferably from 15 to 30 kw/l and that in the overall reaction system is preferably from 3 to 10 W/l.

The product is discharged from the system continuously at any point. It is preferably discharged in the lower region at the bottom of the reactor or, in particular, from the external loop via a catalyst separation unit or without such a unit. This separation unit can be a gravity separator, e.g. a settler, a cross-flow filter or a centrifuge. The catalyst can be separated off from the product and subsequently be returned to the reaction system. The product is preferably discharged while holding back the catalyst. The amine can then be purified by customary and known methods, for example by distillation or extraction.

In the process of the present invention, the mononitro and/or polynitro compound is used in pure form, as a mixture with the corresponding monoamine and/or polyamine, as a mixture with the corresponding monoamine and/or polyamine and water or as a mixture with the corresponding monoamine and/or polyamine, water and a solvent, in particular an alcohol solvent. The aromatic mononitro and/or polynitro compound is introduced into the mixture in finely divided form. The amount of nitro compound which is not fed in at the point provided for according to the present invention is introduced into the jet nozzle, particularly preferably into the mixing zone of the nozzle.

Preference is given to using aromatic nitro compounds having one or more nitro groups and from 6 to 18 carbon atoms, for example nitrobenzenes such as o-, m-, p-nitrobenzene, 1,3-dinitrobenzene, nitrotoluenes such as 2,4-, 2,6-dinitrotoluene, 2,4,6-trinitrotoluene, nitroxylenes such as 1,2-dimethyl-3-, 1,2 dimethyl-4-, 1,4-dimethyl-2-, 1,3-dimethyl-2-, 2,4-dimethyl-1- and 1,3-dimethyl-5-nitrobenzene, nitronaphthalenes such as 1-, 2-nitronaphthalene, 1,5 and 1,8-dinitronaphthalene, chloronitrobenzenes such as 2-chloro-1,3-, 1-chloro-2,4-dinitrobenzene, o-, m-, p-chloronitrobenzene, 1,2-dichloro-4-, 1,4-dichloro-2-, 2,4-dichloro-1- and 1,2-dichloro-3-nitrobenzene, chloronitrotoluenes such as 4-chloro-2, 4-chloro-3-, 2-chloro-4- and 2-chloro-6-nitrotoluene, nitroanilines such as o-, m-, p-nitroaniline; nitroalcohols such as tris(hydroxymethyl)nitromethane, 2-nitro-2-methyl-, 2-nitro-2-ethyl-1,3-propanediol, 2-nitro-1-butanol and 2-nitro-2-methyl-1-propanol, and also any mixtures of two or more of the nitro compounds mentioned, in the process of the present invention.

In the process of the present invention, preference is given to hydrogenating aromatic nitro compounds, preferably mononitrobenzene, methylnitrobenzene or methylnitrotoluene and in particular 2,4-dinitrotoluene or its industrial mixtures with 2,6-dinitrotoluene, where these mixtures preferably contain up to 35 percent by weight, based on the total mixture, of 2,6-dinitrotoluene with proportions of from 1 to 4 percent of vicinal DNT and from 0.5 to 1.5% of 2,5- and 3,5-dinitrotoluene, to form the corresponding amines.

The process of the present invention can be used particularly advantageously in the hydrogenation of dinitrotoluene isomers to form the corresponding toluenediamine derivatives (TDA). The formation of high molecular weight, tar-like by-products, which in the processes of the prior art led to yield losses and to conglutination and thus to premature deactivation of the catalyst, was able to be suppressed virtually completely. As a result, the purification of the TDA is less complicated than in the processes of the prior art.

The hydrogenation of the dinitrotoluene can be carried out in solution. As solvent, use is made of the materials customary for this purpose, in particular lower alcohols, preferably ethanol. The hydrogenation is preferably carried out in the absence of solvents. This has the advantages that the volume of the reaction mixture is lower, which makes it possible for the reactor and the pumps and pipes to be made smaller, that secondary reactions between the solvent and the starting materials are ruled out and that the work-up of the end products is simplified.

The process of the present invention is carried out using the hydrogenation catalysts which are known per se for aromatic nitro compounds. It is possible to use homogeneous and/or in particular heterogeneous catalysts. The heterogeneous catalysts are used in a finely divided state and are present as a fine suspension in the reaction mixture. Useful catalysts are metals of transition group VIII of the Periodic Table, which may be applied to support materials such as activated carbon or oxides of aluminum, of silicon or other materials. Preference is given to using Raney nickel and/or supported catalysts based on nickel, palladium and/or platinum.

As a result of the individual reactants being dispersed and the other reaction parameters, intensive mixing of all components and high mass transfer coefficients and high phase interface areas per unit volume are achieved. The installation of the cooling tubes in the reactor parallel to the reactor walls results in there being virtually no temperature gradients within the contents of the reactor. Avoidance of local overheating results in secondary reactions being suppressed significantly and catalyst deactivation being largely avoided. Consequently, high space-time yields and high selectivities are achieved even at low catalyst concentrations.

As stated above, the process of the present invention is particularly useful for the hydrogenation of dinitrotoluene to toluenediamine. It is precisely in this reaction that pronounced secondary reactions to form tar-like constituents occur in processes of the prior art. The preparation of toluenediamine by the process of the present invention is carried out at the abovementioned temperatures and pressures customary for the preparation of aromatic amines.

The process of the present invention has a number of advantages. An improvement is achieved in the distribution of the starting materials in the reaction mixture, which leads to low contents of by-products and low deactivation of the catalyst. The nitroaromatics are reacted more completely, i.e. the concentration of nitroaromatics at the outlet of the reactor decreases significantly. This makes it possible to increase the space-time yield in the reactor. Compared to the process described in WO 00/35852, there is a further significant reduction in the amount of nitroaromatics in the end product. Surprisingly, aging of the catalyst is also reduced. The residence time of the nitroaromatics in the reactor is increased, which in principle also makes it possible to reduce the catalyst concentration.

The introduction of the hydrogen according to the present invention enables the energy input into the reactor to be reduced, since the hydrogen increases the gas content and thus the mass transfer performance in the annular space of the reactor and its buoyancy stabilizes the internal loop flow. The energy input through the jet nozzle and thus also the quantity of the external circuit can be significantly reduced. Apart from the energy saving, this also leads to reduced mechanical stress and thus to a longer catalyst life.

The invention is illustrated by the following example.

EXAMPLE 1

A cylindrical reactor provided with an external circuit with pump, a nozzle, an impingement plate in the lower part of the reactor and a concentric plug-in tube is used. The reaction volume of the reactor is about 12 m$^3$. The reactor is provided with 350 parallel Field tubes (4) which correspond to a total cooling area of about 300 m$^2$. The amount of cooling water fed into the Field tubes was 250 m$^3$/h, and the temperature of the cooling water fed into the Field tubes was 50° C.

7 t/h of a dinitrotoluene melt were fed via a distributor ring having 12 outlet openings each having a diameter of 5 mm into the liquid reaction mixture above the impingement plate. A pressure of 25 bar was maintained in the reactor by simultaneous introduction of 5200 standard m$^3$/h of hydrogen into the gas space of the reactor. Hydrogen was fed in through a distributor ring which was installed below the impingement plate and had 30 holes each having a diameter of 8 mm. To maintain the loop flow, a volume flow of 500 m$^3$/h was circulated around the external product circuit. The pressure in the reaction nozzle was about 2.5 bar above that in the gas space of the reactor, and the power input was 3.5 kW/m$^3$. The reaction proceeded under virtually isothermal conditions, since the heat of reaction evolved was removed at the location where it was generated. The maximum temperature in the lower third of the reactor was 125° C. At the same time, 4.64 t/h of a corresponding diaminotoluene mixture and 2.74 t/h of water were taken continuously from the reactor via a crossflow filter installed in the external circuit so as to hold back the catalyst. This corresponded to a space-time yield of 400 kg of amine mixture/(m$^3$·h). The yield of diamine based on dinitrotoluene used was >99%. On work-up by distillation, 0.15% of low-boiling by-products ("low boilers") and 0.75% of tar-like products ("high boilers") were obtained. The amount of nitro or aminonitro compounds present in the product was below the detection limit of 10 ppm. No appreciable deactivation of the hydrogenation catalyst employed was observed under the operating conditions described above even after a reaction time of 100 h.

We claim:

1. A process for preparing amines, comprising hydrogenating the corresponding nitroaromatics in a vertical reactor whose length is greater than its diameter, and which has in its upper region a downward-directed jet nozzle via which the reaction mixture, and, if desired, a part of the starting materials is introduced, has an outlet at any point on the reactor via which the reaction mixture is conveyed in an external circuit by means of a transport device back to the jet nozzle and has a flow reversal in its lower region, wherein at least a part of the hydrogen and/or nitroaromatic starting materials used, is fed into the liquid phase of the reactor in such a way that they travel upward in the liquid phase.

2. The process as claimed in claim 1, wherein the nitroaromatics are introduced above the flow reversal.

3. The process as claimed in claim 1, wherein the reactor has an impingement plate arranged perpendicular to the reactor wall in its lower part.

4. The process as claimed in claim 1, wherein a concentric plug-in tube is installed in the reactor parallel to the reactor wall.

5. The process as claimed in claim 1, wherein the nitroaromatics are fed into the reactor between an impingement plate and a plug-in tube.

6. The process as claimed in claim 1, wherein the hydrogen is fed in between the bottom of the reactor and a plug-in tube.

7. The process as claimed in claim 1, wherein part of the hydrogen used, is fed into the external circuit of the reactor.

8. The process as claimed in claim 1, wherein hydrogen is fed into the external circuit of the reactor in such an amount that the reaction mixture in the external circuit has a gas content in the range from 3 to 15% by weight.

9. The process as claimed in claim 2, wherein a concentric plug-in tube is installed in the reactor parallel to the reactor wall.

10. The process as claimed in claim 2, wherein the nitroaromatics are fed into the reactor between an impingement plate and a plug-in tube.

11. The process as claimed in claim 3, wherein the nitroaromatics are fed into the reactor between the impingement plate and a plug-in tube.

12. The process as claimed in claim 2, wherein the hydrogen is fed in between the bottom of the reactor and a plug-in tube.

13. The process as claimed in claim 3, wherein the hydrogen is fed in between the bottom of the reactor and a plug-in tube.

14. The process as claimed in claim 4, wherein the hydrogen is fed in between the bottom of the reactor and the plug-in tube.

15. The process as claimed in claim 2, wherein part of the hydrogen used, is fed into the external circuit of the reactor.

16. The process as claimed in claim 3, wherein part of the hydrogen used, is fed into the external circuit of the reactor.

17. The process as claimed in claim 4, wherein part of the hydrogen used, is fed into the external circuit of the reactor.

18. The process as claimed in claim 5, wherein part of the hydrogen used, is fed into the external circuit of the reactor.

19. The process as claimed in claim 2, wherein hydrogen is fed into the external circuit of the reactor in such an amount that the reaction mixture in the external circuit has a gas content in the range from 3 to 15% by weight.

20. The process as claimed in claim 3, wherein hydrogen is fed into the external circuit of the reactor in such an amount that the reaction mixture in the external circuit has a gas content in the range from 3 to 15% by weight.

* * * * *